United States Patent
Arb et al.

(10) Patent No.: US 6,244,030 B1
(45) Date of Patent: Jun. 12, 2001

(54) PROCESS AND DEVICE FOR MONITORING THE QUALITY OF YARNS

(75) Inventors: Werner Arb, Uster (CH); Christoph Färber, Korschenbroich (DE)

(73) Assignee: Zellweger Luwa AG, Uster (CH)

( * ) Notice: Subject to any disclaimer, the term of this patent is extended or adjusted under 35 U.S.C. 154(b) by 0 days.

(21) Appl. No.: 09/155,307

(22) PCT Filed: Mar. 12, 1997

(86) PCT No.: PCT/CH97/00103

§ 371 Date: Feb. 24, 1999

§ 102(e) Date: Feb. 24, 1999

(87) PCT Pub. No.: WO97/36032

PCT Pub. Date: Oct. 2, 1997

(30) Foreign Application Priority Data

Mar. 27, 1996 (CH) .................................................. 792/96

(51) Int. Cl.⁷ .................................................. D01H 13/26
(52) U.S. Cl. .................................. 57/264; 57/265; 73/159
(58) Field of Search ........................ 57/264, 265; 73/159

(56) References Cited

U.S. PATENT DOCUMENTS

| | | | |
|---|---|---|---|
| 4,051,722 | * 10/1977 | Feller | 73/160 |
| 4,168,604 | * 9/1979 | Mannhart | 57/265 |
| 4,246,748 | * 1/1981 | Artzt et al. | 57/265 |
| 4,491,831 | * 1/1985 | Sakai et al. | 57/265 |
| 4,924,406 | * 5/1990 | Bergamini et al. | 57/264 |
| 5,119,308 | * 6/1992 | Samoto | 364/470 |
| 5,371,584 | 12/1994 | Scheinhütte | 356/238 |
| 5,414,520 | 5/1995 | Joss et al. | 356/430 |
| 5,497,335 | * 3/1996 | Hoeller | 364/470 |
| 5,521,395 | 5/1996 | Hensel et al. | 250/562 |
| 5,537,811 | * 7/1996 | Pidoux et al. | 57/265 |
| 5,592,849 | * 1/1997 | Nakade et al. | 73/160 |
| 5,748,481 | * 5/1998 | Nakade | 57/264 |
| 5,768,938 | 6/1998 | Schilling et al. | 73/160 |
| 5,834,639 | * 11/1998 | Meier et al. | 73/159 |
| 5,950,411 | * 9/1999 | Simon | 57/264 |

FOREIGN PATENT DOCUMENTS

| | | |
|---|---|---|
| 477573 | 10/1969 | (CH) . |
| 674 379 | 5/1990 | (CH) . |
| 0 643 294 | 3/1995 | (EP) . |
| 0 652 432 | 5/1995 | (EP) . |
| 0 685 580 | 12/1995 | (EP) . |
| 63-092738 | 4/1988 | (JP) . |
| 6-322621 | 11/1994 | (JP) . |
| 93/13407 | 7/1993 | (WO) . |

* cited by examiner

*Primary Examiner*—William Stryjewski
(74) *Attorney, Agent, or Firm*—Burns, Doane, Swecker & Mathis L.L.P.

(57) ABSTRACT

The invention relates to a process and device for monitoring the quality of yarns. In order to differentiate extraneous materials in a yarn section front the yarn itself and from other extraneous materials more effectively, a signal (10) derived from the yarn (8) must be classified in a classification field (16). On the basis of that classification, the extraneous materials contained in the yarn and their types can be determined.

5 Claims, 4 Drawing Sheets

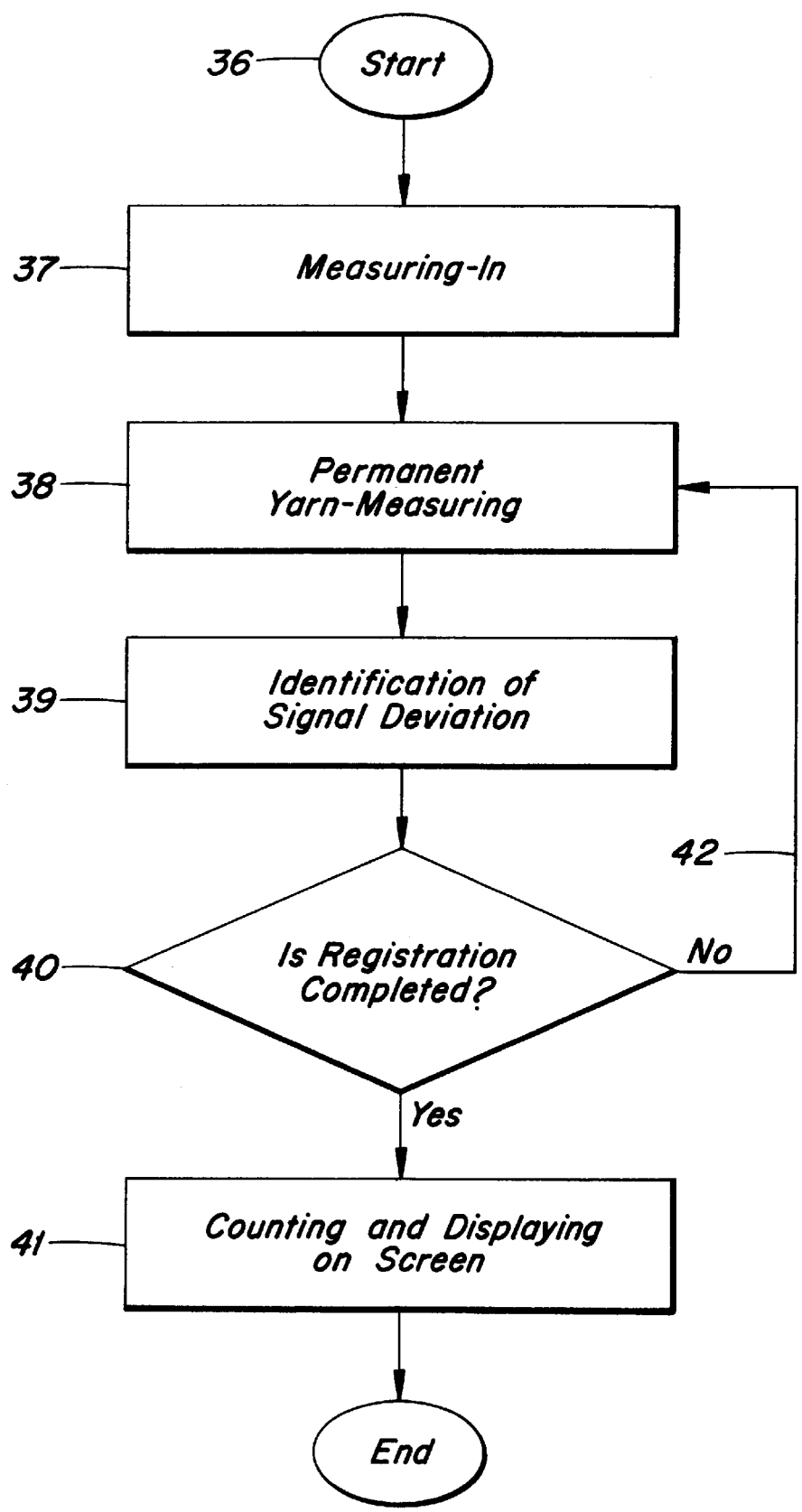

PROCESS AND DEVICE FOR MONITORING THE QUALITY OF YARNS

BACKGROUND OF THE INVENTION

The invention relates to a process and device for monitoring the quality of yarns.

A device for yarn-clearers is known from CH-477573, for example, with the aid of which it is possible to perform monitoring of the quality of yarns by cutting out defects which exceed certain limit values. In that instance, a defect is characterized by the fact that it exceeds, or falls below, the average diameter of the yarn over a finite length. Certain defects are cut out by a knife and the yarn is then spliced again. In order to activate a cutting knife, a so-called clearing limit is fixed, against which all defects are measured. Those defects which exceed the clearing limit are cut out by the cutting knife. The clearing limit is composed of points, each of which is characterized by a certain deviation from the average diameter, and by a certain length of a portion of yarn. Known clearing limits have a continuous course or else a discontinuous course (with discontinuities). However, they usually have the effect that deviations from the diameter which are major ones but of only brief length are not cut out, whereas minor deviations of great length are cut out. It is known practice to locate such clearing limits over a classifying field, under which circumstances the class limits and the clearing limit do not always coincide. However, such a clearing limit always divides the space or an area into two regions: a region outside the clearing limit for intolerable defects and a region inside the clearing limit for tolerable defects.

A disadvantage of these known devices can be seen, for example, in the fact that, in addition to the irregularities in the yarn per se, foreign substances which are spun into the yarn and bring about a change in diameter, are cleared out in the same way as ordinary thick or thin points in the yarn. This means that it is not possible to distinguish between the various foreign substances which are encountered, such as foreign bodies, shell parts, fibers of other colors, hairs, knots, etc. Thus, it is likewise not possible to selectively cut out individual types of foreign substances. Known devices are equipped with sensors which make it possible to detect the diameter or the mass of a portion of yarn and, from it, to monitor the uniformity of the mass or diameter, viewed over the length of the yarn, or even to identify foreign substances in the yarn in a general manner. An electrical signal, which is correlated with a portion of yarn, is usually produced in the sensor. However it is difficult and unreliable to deduce therefrom whether a certain foreign body is now contained in the portion of yarn. It is possible to identify the presence of a foreign body, but impossible to determine its nature.

There is therefore no possibility of distinguishing between yarn and foreign substance, or between various kinds of foreign substances in the yarn. Shell parts in the yarn are usually removed from the latter by further processing, for example chemical aftertreatment for bleaching purposes, as they can be very successfully identified later in the woven cloth. They are often immediately conspicuous, or else become apparent through the fact that they do not take on color, or do so only inadequately, during the dyeing process.

SUMMARY OF THE INVENTION

An object of the present invention is to provide a process and device with the aid of which certain foreign substances in a portion of yarn can be accurately distinguished from the yarn and from other foreign substances.

This object is achieved through the fact that the yarn is optically scanned by incident light and an electrical signal is first of all obtained therefrom. A classifying field which has a number of threshold values for the amplitude, and a number of threshold values for the length/duration, of a portion of the electrical signal is predetermined beforehand for the values of the electrical signal. The signal can then be compared with all the threshold values. Classes are formed by combinations of four threshold values. It is then ascertained, in respect of each portion of yarn, to which class it belongs and it can he ascertained, starting from the class affiliation, what kind of any foreign substances occur in the yarn. It is then possible to separate out, or simply count, portions of yarn of the same class.

The advantages achieved through the invention can be seen in the fact that it is thereby possible to carry out a correlation between the yarn and individual kinds of foreign substances, on the one hand, and the electrical signal which is present, on the other. For example it is possible, starting from the knowledge that shell parts result in particularly short defects, to predetermine that defects which are classified in one or more fields which are correlated with the shortest portions, must just be shell parts. In just the same way, it is possible to predetermine that, for example, defects which are correlated with fields which delimit average lengths and average changes in diameter, must be leaf or stem residues of the cotton plant, etc.

BRIEF DESCRIPTION OF THE DRAWINGS

The invention will be explained in greater detail below with the aid of an example and with reference to the accompanying drawings, in which:

FIG. 5 shows a flow chart for the process according to the invention.

DETAILED DESCRIPTION OF THE DRAWINGS

Figure 1:
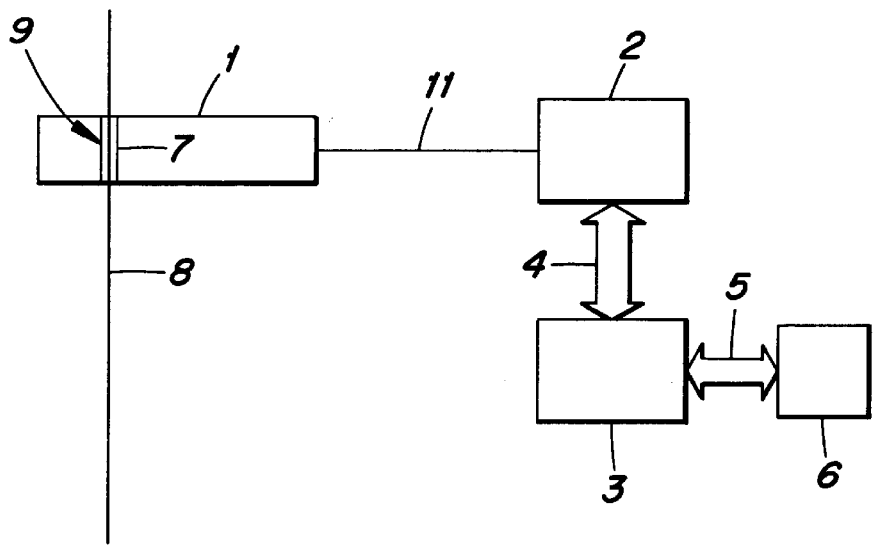
FIG. 1 shows a diagrammatic representation of the device according to the invention.

The device according to the invention shown in FIG. 1 essentially consists of a measuring head 1 of a constructional type known per se, an evaluating unit 2 and a control apparatus 3 which is connected to the evaluating unit 2 via a bus 4. The control apparatus 3 is connected, via another bus 5, to an indicating and operating unit 6 which may be part of a spinning or spooling machine. The measuring head 1 has a measuring gap 7 in which a yarn 8 is moved through in its longitudinal direction by means which are known per se and are therefore not represented in any greater detail here, and is subjected to detection in portions. The measuring head 1 preferably has a measuring system 9 which adjoins the measuring gap 7 and operates optically, in particular with incident light. This means that the light reflected at the yarn is received in a sensor in known manner and converted to an electrical signal. Such measuring systems are known per se and are described more accurately in Patent Application WO 93/13407 for example.

Figure 2:
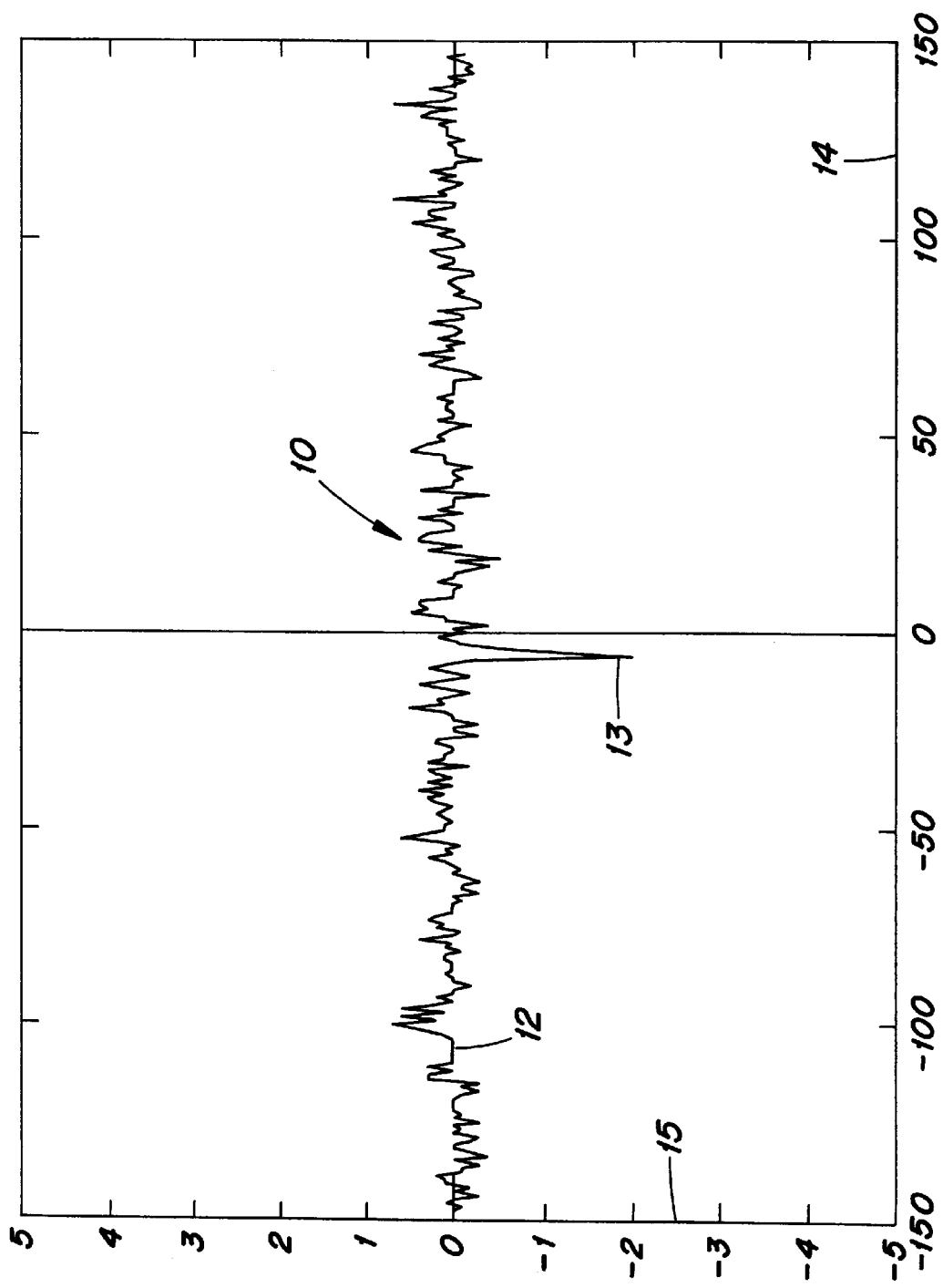
FIG. 2 shows a representation of a signal from the device according to FIG. 1, FIGS. 3 and 4 each show a representation of a classifying matrix.

FIG. 2 shows an electrical signal 10, as emitted by the measuring head 1, for example via a line 11 (FIG. 1) which connects the control apparatus 3 and the measuring head 1 to one another. The signal 10 is plotted above a horizontal axis 14 on which there are indicated units of length which relate to the yarn 8. Plotted on a vertical axis 15 are, for example, values of an electrical voltage. This signal 10 essentially consists of small, insignificant deflections which are caused by small irregularities in the surface of the yarn 8. This can also be summed up by the term "background noise". The signal 10 is centered around a zero line 12, 13 designates a projecting signal deviation which makes it possible to infer a particular event. In this case, the said event is a shell part which, for example, adhered to a fibre and has been spun into the yarn as a result of the spinning operation. Shell parts are solid residues of the cotton plant (for example parts of seeds or seed capsules) which are present in the yarn in severely comminuted form as a result of mechanical stressing during the treatment process (for example in the course of spinning). They are, on average, about 0.5 mm in size and compact, for example punctiform, in shape. In this case, the signal deviation has occurred, for example, as a result of a reduced reflection of the aforesaid incident light, which reduced reflection is attributable, for example, to the dark color of such shell parts.

Figure 3:
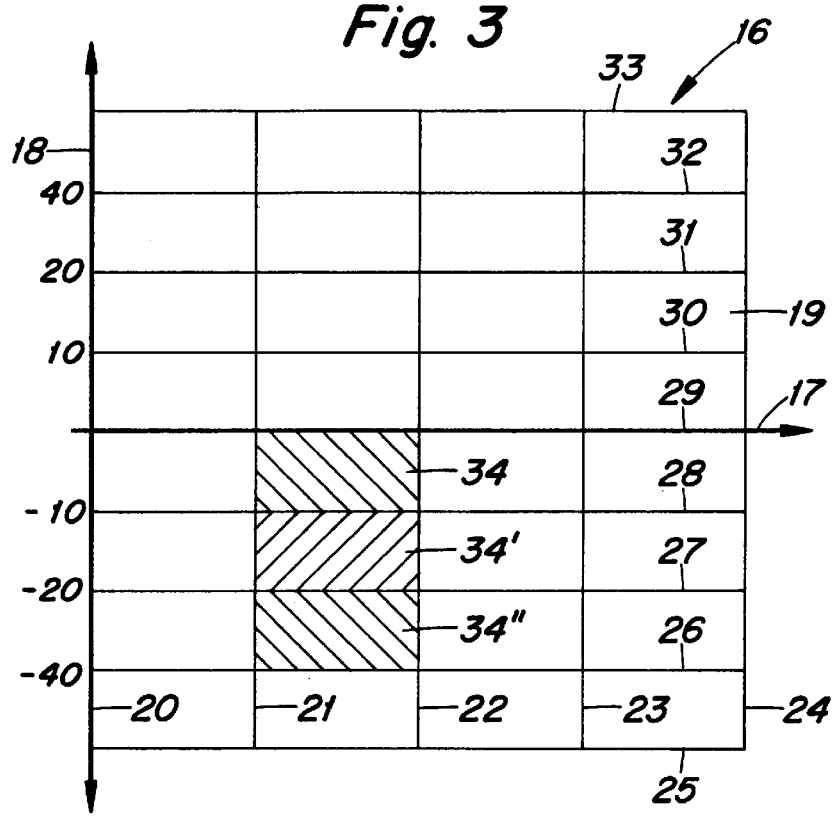

FIG. 3 shows a classifying field or classifying matrix 16 which has an axis 17, along which the length of portions of yarn is plotted in millimeters, and an axis 18, along which values for the deflection or amplitude of the electrical signal 10 are plotted. In this case, these are values which indicate the measure of the reflection in percentages. The classifying matrix 16 shown has 32 fields 19 which are delimited by lines 20 to 24 and 25 to 33. These lines 20 to 33 also have the significance of threshold values with which the signal 10 is compared. An individual field 19, such as, in particular, the field 34 here, is always delimited by four lines, in this case the lines 21, 22, 28 and 29, or four threshold values. The distance of the lines 20 to 24 from one another may correspond, for example, to a length of 1 mm on the yarn 8. A field or group of fields, in this case the fields 34, 34' and 34", defines classes for signal deviations, which point, for example, to the existence of leaf or stem residues of the cotton in the yarn.

Figure 4:
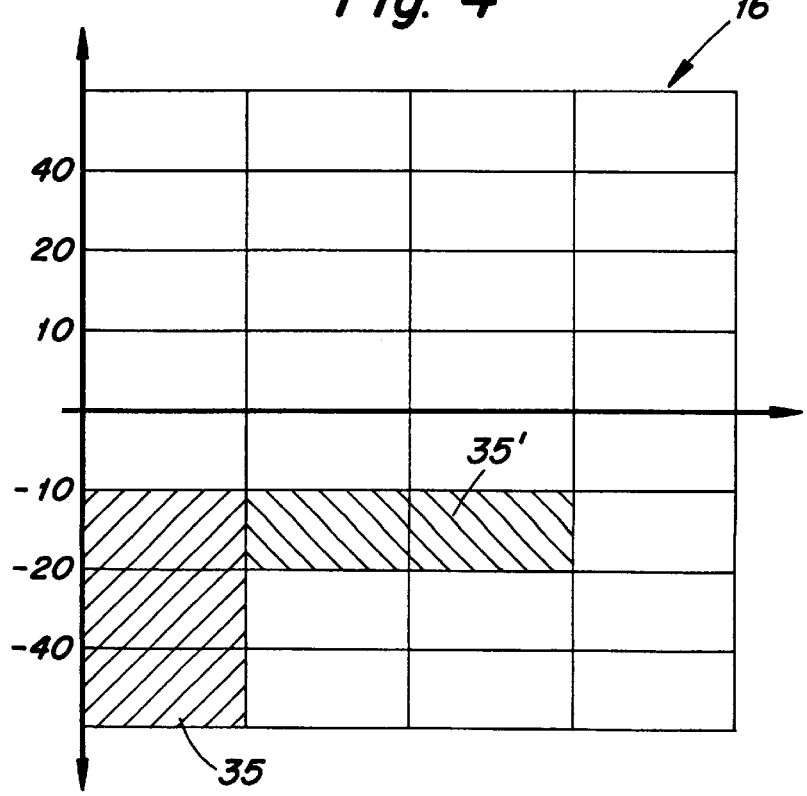

FIG. 4 shows, once again, the classifying field 16 in which there is plotted a field 35 which relates to such lengths and deflections of the signal 10 as are characteristic of shell parts. Signals which can be correlated with another field 35' indicate that the contaminant which is present is jute residues from bale packaging. These jute residues are usually broken up to form fibers.

FIG. 5 shows a flow chart for the process according to the invention. With it, the way in which the device according to FIG. 1 works is to be explained below. The process is triggered, for example, by pressing a start button in the operating unit 6, which is indicated by the step 36. This leads to the program being loaded from the control apparatus 3, which consists of a computer (PC) for example, into a processor in the evaluating unit 2. Then a measuring-in operation 37 begins.

The measuring-in operation 37 is performed while a piece of yarn some meters in length is moved through the measuring gap 7. This serves the purpose of obtaining initial measurement values from the yarn 8, for example for the reflection, calculating an average value therefrom and setting the zero line 12 (FIG. 2) to the said mean value. Then begins the actual measuring operation, the permanent yarn-measuring operation 38.

In the permanent yarn-measuring operation 38, the yarn 8 is drawn through the measuring gap 7 and a signal 10 (FIG. 2) is produced. The signal 10 is produced as a result of periodic scanning of the continuously occurring values for the reflection of the light in the measuring head 1. Every time the yarn 8 has moved forward by, for example, 2 mm in the measuring gap 7, a measurement value is detected again and the latter is compared with all the threshold values of the classifying field 16, that is to say with all the values which are represented by the lines 20 to 33. This is the identification of a signal deviation 39 and takes place in the processor of the evaluating unit 2. However, the program in the processor supplies still further predeterminations. If, in particular, threshold values corresponding to the lines 28 or 30 are exceeded, the corresponding portions of the signal are read into a memory in the processor and remain there until the latest value exceeds these lines 28 or 30 again in the other direction. The time during which such a value stays in the memory corresponds to a length such as is plotted on the axis 17 in FIG. 3, and is then measured at threshold values which are represented by lines 21 to 24. For example, a portion of the signal which exceeds the threshold value according to line 31 but does not exceed the line 32 and remains in the memory for a period of time such that threshold values according to the lines 21 and 22, but not 23, are exceeded, results in a yarn defect which is to be classified in field 34. If such a defect is discovered, it is registered, for example through the fact that a counter is activated which counts the defects correlated with this field 34, or else a knife disposed in a manner adjacent to the measuring head 1 is activated. These are the operations which are correlated with a step 40 which completes the registration and with a step 41 which relates to a counting operation. The feeding-back operation 42 further indicates that these operations are repeated constantly and for each scanning operation or each measuring cycle.

Other foreign substances can be ascertained on the basis of the classified signal deviations. Thus, it is possible to start from the fact that foreign substances which have little contrast in relation to the yarn or to the light from the light source with which they are illuminated, occupy classes or fields which relate to small signal deviations, corresponding in FIG. 3, for example, to the fields which lie between the axis 17 and the line 28. As an example, mention may be made of a light-colored polypropylene which originates from packaging. Signals from foreign substances which produce a correspondingly large amount of contrast are to be found in fields between the lines 25 and 27 and can be correlated, for example, with clothing residues having strong colors.

Figure 6:
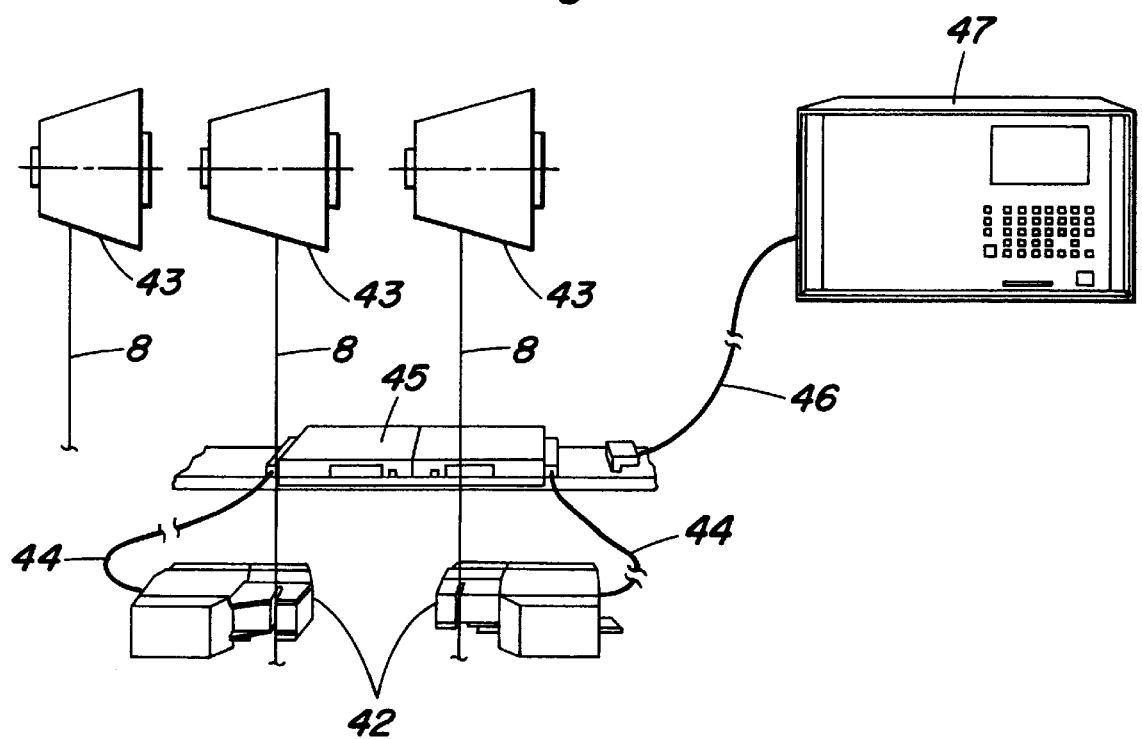
FIG. 6 shows a view of the device.

FIG. 6 shows a view of a device according to the invention, in which—measuring heads 42 for identifying foreign substances are disposed directly on a spinning machine or spooling machine. The measuring heads 42 have the yarn 8 running through them shortly before it is wound onto a spool 43. The measuring heads 42 are connected, via lines 44, to an evaluating unit 45 which, in turn, is connected, via a bus 46, to a central control, operating and indicating unit 47 for a number of measuring heads. In this way and with this device, it is possible to identify, even on the spinning or spooling machine, the nature and type of the foreign substances occurring in a portion of yarn, and to distinguish them from one another on the basis of the signal from the measuring head.

What is claimed is:

1. A process for obtaining information concerning a yarn that may have therein pieces of different types of foreign matter of different lengths and light reflectivity, comprising:

establishing a classifying matrix having a plurality of fields each representing a range of length values and a range of reflected light values, with certain of said fields being correlated with the typical lengths and reflected light values of different types of foreign matter found in yarns, passing the yarn lengthwise through a detector and periodically producing an electrical signal indicating a value for the amount of light being reflected from a yarn portion having a piece of foreign matter therein and indicating the lengthwise extent of such foreign matter in said yarn portion;

comparing said electrical signals with said classifying matrix to classify the signals from yarn portions containing pieces of different types of foreign matter in fields correlated respectively with the typical lengths and reflected light values of the different types of foreign matter found in yarns; and initiating an action in response to the classification of a signal into a predetermined one of said fields.

2. A process according to claim 1, wherein said action is a counting action for events falling within said one of said fields.

3. A process according to claim 1, wherein said action comprises removing from the yarn the yarn portions which correspond to the signals classified in said one of said fields.

4. A process according to claim 1, wherein a field in said classifying matrix corresponds to signals which have amplitudes falling within a predetermined range correlating with the amount of light reflected by a particular type of foreign matter and which have durations falling within a predetermined range correlating with a length characteristic of pieces of the same type of foreign matter.

5. A process according to claim 1, wherein said classifying matrix includes thirty two of said fields.

* * * * *